United States Patent
Higashi

[11] Patent Number: 5,991,031
[45] Date of Patent: Nov. 23, 1999

[54] OPTICAL DENSITY MEASURING APPARATUS

[75] Inventor: Noboru Higashi, Neyagawa, Japan

[73] Assignee: Kurashiki Boseki Kabushiki Kaisha, Okayama, Japan

[21] Appl. No.: 09/179,821

[22] Filed: Oct. 28, 1998

[30] Foreign Application Priority Data

Oct. 29, 1997 [JP] Japan ................................. 9-296903

[51] Int. Cl.⁶ .................................................. G01B 9/02
[52] U.S. Cl. ........................................... 356/346; 356/306
[58] Field of Search ........................... 356/346, 300, 356/306

[56] References Cited

U.S. PATENT DOCUMENTS

| | | | |
|---|---|---|---|
| 4,999,010 | 3/1991 | Mattson et al. | 356/346 |
| 5,276,500 | 1/1994 | Koehler | 356/346 |
| 5,305,077 | 4/1994 | Grego et al. | 356/346 |

FOREIGN PATENT DOCUMENTS

| | | |
|---|---|---|
| 59-107241 | 6/1984 | Japan . |
| 3-59445 | 3/1991 | Japan . |
| 3-223654 | 10/1991 | Japan . |
| 4-1556 | 1/1992 | Japan . |
| 5-332933 | 12/1993 | Japan . |
| 7-306139 | 11/1995 | Japan . |

*Primary Examiner*—Robert H. Kim
*Attorney, Agent, or Firm*—Wenderoth, Lind & Ponack, L.L.P.

[57] ABSTRACT

An optical system for measuring an optical density of a sample in which homogeneity of light employed for measuring the density thereof is secured by including optical information upon a light source uniformly inside a measurement space about an optical axis therein even if the fluctuation occur in the light source in the system. A beam of light emitted from the light source and then focused on an interference filter is transformed into a parallel light through a collimator lens, and the parallel light is then split into two parallel pencils of light by an optical mask. The parallel light uniformly includes the optical information upon the light source. A reference cell is placed in a first split parallel pencil of light, and a sample cell is placed in a second split parallel pencil of light. The lights that have passed through the two cells are focused on an optical receiver by a focusing lens.

6 Claims, 7 Drawing Sheets

OPTICAL DENSITY MEASURING APPARATUS

BACKGROUND OF THE INVENTION

1. FIELD OF THE INVENTION

The present invention generally relates to an optical density measuring apparatus for securing homogeneity of infrared measuring light which has a pair of cells being a reference cell and a sample cell in an infrared optical system thereof and which finds an optical density of a sample on a basis of a ratio between a pair of intensities of the infrared measuring lights passing through the pair of cells, and particularly relates to the optical density measuring apparatus therefor with a double-beam optical system which transforms the infrared measuring light emitted from a light source into a parallel infrared measuring light by a collimator lens, splits the parallel measuring light into two split parallel pencils of light, and makes the first pencil of light and the second pencil of light pass through the reference cell and the sample cell, respectively.

2. DESCRIPTION OF THE RELATED ARTS

A variety of types of optical density measuring apparatuses have conventionally been provided. The types of optical density measuring apparatuses are generally classified by their optical paths, or pencils of measuring light, into two types: a type with a single-beam optical system and a type with a double-beam optical system. The former type, namely, the type with the single-beam optical system, which has been conventionally popularized for a long time, has a construction in which a cell is positioned in one pencil of light travelling from a light source to an optical receiver. With the construction, the cell is filled up preparatorily with pure water as a reference liquid, and the quantity of transmitted light of the measuring light that passes through the pure water is detected beforehand by the optical receiver. Then, after replacing the pure water inside the cell with a sample, the quantity of transmitted light of the measuring light that passes through the sample is detected, and the density of the sample is found or calculated from the ratio between the quantities of both of the transmitted measuring lights.

This type of optical density measuring apparatus with the single-beam optical system, which employs the single optical path or pencil of light, has an advantage that an optical identicalness is maintained or assured at time of measuring the reference cell and at time of the sample cell, except for the density of the sample inside the cell.

However, a blank calibration (zero-calibration) of the optical density measuring apparatus belonging to this type has to be periodically executed in order to guarantee the identicalness thereof for a long term, and a user has to take a trouble to replace the sample with pure water for the calibration. As a result, this leads to a problem of reduction in measurement efficiency of measuring the optical density of the sample.

Also, an additional device or structure for the replacement of the sample with the pure water is indispensable, and this leads to another problem of high cost of the apparatus.

Furthermore, in case that even a little amount of the sample remains inside the cell when replacing the sample with the pure water at time of executing the blank calibration, the reliability of the blank calibration accuracy is impaired.

Meanwhile, there has been suggested an apparatus of the type with the single-beam optical system which employs a cell called a cylinderical type variable-length cell (refer to Japanese Laid-Open Patent Publication No. 4-1556). This cylinderical type variable-length cell changes the position of a piston therein to allow the thickness of a cylinder space, in which a sample is put, to be changed into a reference cell length and a sample cell length. This apparatus has an advantage that it necessitates no pure water for the blank calibration; however, it is very difficult to maintain the piston at a predetermined position with high accuracy for a long period. Therefore, the apparatus has not yet been put into practical use.

On the other hand, the apparatus of the type with the double-beam optical system is intended for solving the aforementioned problems of the type with the single-beam optical system, thereby obviating the need to carry out the blank calibration employing the pure water.

The type with the double-beam optical system includes a type of apparatus in which a measurement light emitted from a light source is directly split into two optical paths or pencils of light from the beginning, in which a reference cell and a sample cell are positioned in the first pencil of light and the second pencil of light, respectively, in which identical samples are put in both of the cells, and in which the lights that have passed through the cells are received by an optical detector or optical receiver (refer to Japanese Laid-Open Patent Publication No. 3-223654). This apparatus has an advantage that it necessitates no pure water for blank calibration, and an advantage that both of the cells are stationary (or fixed) and are provided with no movable portion.

However, the apparatus directly splits the measuring light from the light source into the two partial lights (i.e. two pencils of light) even though the light source is identical. Therefore, the homogeneity or identicalness of the two diverged optical paths, or pencils of light, is not guaranteed at all. Therefore, a calibration curve must be prepared and made every time the light source is aged, or every time the light source itself is changed. As is well known, the preparation and making of the calibration curve is a troublesome work requiring many hours and much burden.

Therefore, assuring the homogeneity, or identicalness, of the optical paths, or pencils of light, to be used for the measurement of both of the reference cell and the sample cell is absolutely necessary for the improvement of the accuracy of the measurement thereof.

As another conventional apparatus of the type with the double-beam optical system, which seems to somewhat solve the aforementioned problem, there can be enumerated an apparatus disclosed in Japanese Laid-Open Patent Publication No. 5-332933. The essential part of this apparatus is schematically shown in FIGS. 1 and 2.

This apparatus has an optical system including an infrared light source "O", a shutter "S" for taking part of light out from the light source "O", a mask "M" having two apertures "M1" and "M2", a collimator lens "L2", a reference cell "C1", a sample cell "C2", an interference filter (not shown), a focusing lens (not shown), and an optical receiver or optical detector (not shown). In this optical system, an infrared measuring light emitted from the light source "O" pass limitedly through a region of an opening "S1" of the shutter "S" located ahead. In the figures, the opening "S1" is located in an upper position.

In the figures, the infrared measuring light that has passed through the opening "S1" further passes through the first aperture "M1" of the mask "M", the travelling pencil of the infrared measuring light is transformed into a parallel pencil of light by the collimator lens "L2," and then the parallel pencil of light passes through the reference cell C1.

On the other hand, when the opening "S1" of the shutter "S" moves to a lower position (not shown), the infrared measuring light emitted from the light source "O" passes through the second aperture "M2" of the mask "M", the travelling pencil of the infrared measuring light is transformed into a parallel pencil of light by the collimator lens "L2," and then the parallel pencil of light passes through the sample cell "C2" (a detailed description about subsequent processing of the transmitted measuring light is omitted below).

In the optical system of the apparatus shown in FIGS. 1 and 2, the two split parallel pencils of light, which are derived from one pencil of light emitted forward from the light source "O," are used as a light that passes through the reference cell "C1" and a light that passes through the sample cell "C2", respectively, by employing at least an identical optical component. Therefore, the homogeneity, or identicalness, of both of the split parallel pencils of light is presumed to be guaranteed considerably.

However, if a measurement with ultrahigh-accuracy is desired, even this apparatus cannot realize a sufficient homogeneity or identicalness of the two split parallel pencils of light employed therein. The reason for this will be described below with reference to FIGS. 1 and 2.

It may be generally considered that, if an identical light source is used, identical fluctuations arise simultaneously in the two parallel pencils of light with respect to a fluctuation in light emission intensity of the light source. However, strictly speaking, the light source has a specified area with respect to the entrance pupil diameter of the optical system. Therefore, the improvement of the accuracy of measurement cannot be realized unless the optical system is constructed by taking into consideration the fact that the optical information of the intensity, and so on, of the infrared measuring light emitted from each luminous point constituting the specified area differs at each luminous point.

The light source "O" shown in FIGS. 1 and 2 includes a filament "O1" that serves as an illuminant. In FIG. 1, the center of the filament "O1" having a specified area, and the point of center of symmetry of the two apertures "M1" and "M2," are both located on an optical axis "P." In this construction, an infrared measuring light emitted from the point of the center "O2" of the filament "O1" is limited by the mask apertures "M1" and "M2," and then the two split measuring lights are made to pass through the collimator lens "L2" so that the two split measuring lights are transformed into two split parallel pencils of light "B1" and "B2" symmetrical relatively to along the optical axis "P." That is, in a certain measurement space of the cell "C," the pencils of light "B1" and "B2" can be regarded as lights with an identical quality.

On the other hand, the infrared measuring light emitted from an end "O3" of the filament "O1" is transformed into two split parallel pencils of light "D1" and "D2" in a similar manner, as shown in FIGS. 1 and 2. As is apparent from the figures, the pencils of light "D1" and "D2" are not symmetrical relatively to the optical axis "P", and are unbalanced. That is, if a pair of apertures on the mask are arranged on the basis of a mere simple conception that only the symmetry of the apertures relative to the optical axis is essential, then the two pencils of light "D1" and "D2" may pass through asymmetrical areas (i.e. areas not symmetrical relative to the optical axis "P") of the measuring space in which the cells "C1" and "C2" are positioned.

A further problem may arise by a positional shift of the filament "O1" when the light source "O" itself is replaced by another one. FIG. 2 shows a state in which the position of the filament "O1" is shifted from the state of FIG. 1. FIG. 2 illustrates a situation where an end "O4" of the filament "O1" is positioned on the center of the optical axis "P". In this case, the other end "O3" of the filament "O1" is largely displaced from the center of the optical axis "P." Therefore, the pencils of light "D1" and "D2" that have been limited by the mask apertures "M1" and "M2" are more largely displaced or shifted from the optical axis "P" in the measuring space.

Under an extreme situation, it is possible that the pencil of light "D2" that passes through the sample cell "C2" may include almost none of the optical information upon the end "O3" of the filament "O1."

Consequently, under such a situation, the two pencils of light have optical information with utterly different qualities when the light source is replaced. Therefore, the relation between the density and the absorbance measured or calibrated on the basis of the optical information prior to the replacement of the light source becomes unusable, which in turn requires a remake (or reconstruction) of the calibration curve with respect to the replaced new light source.

Another problem is a positional nonuniformity of optical penetration characteristics of an interference filter which is employed in this type of spectroscopic apparatus. As a spectroscopic filter to selectively allow a specified wavelength to pass the filter, the interference filter is simple, convenient and thus widely used. However, its spectroscopic spectrum characteristics are not always uniform depending on each interference filter. This nonuniformity thereof is in connection with the problem concerning a manufacturing process of a multilayer deposition film, and even the spectroscopic spectrum characteristics of a plurality of interference filters manufactured through an identical manufacturing process have variations in the peak wavelength and half width thereof. Further, strictly speaking, even in one filter, the spectroscopic penetration spectrums are not necessarily the same, depending on what part of the filter the light passes.

Since the pencil of light is single in the aforementioned conventional type of the apparatus with the single-beam optical system, the positional nonuniformity of the interference filter is similarly included both at the sample measuring stage and at the reference measuring stage, causing no such problem as described above. However, in case that the pencil of light is split into parts and that a difference in spectroscopic spectrum between both the optical paths is caused, a fatal error arises in the measurement result.

Therefore, it is an important technical object how the positional nonuniformity of the spectroscopic spectrum is allowed to be uniformly included in both of the pencils of light.

SUMMARY OF THE INVENTION

Accordingly, it is an object of the present invention to provide an optical density measuring apparatus in which the homogeneity or identicalness of the measuring lights is secured so that the optical information upon the light source is uniformly included in the measuring space about the optical axis, even if a fluctuation occurs in the light source therein.

It is another object of the present invention to provide the optical density measuring apparatus in which the homogeneity or identicalness of the measuring lights is secured even if there is a positional nonuniformity in the spectroscopic penetration spectrum of the interference filter employed for the spectroscopic filter, so that the nonuniformity of the penetration spectrum is uniformly included in the measuring space about the optical axis.

In accomplishing these and other objects of the present invention, there is provided an optical density measuring apparatus comprising: a light source for emitting an infrared ray as a measuring ray; an interference filter for selecting a predetermined wavelength of the measuring ray that passes through the interference filter; a first lens for focusing the measuring ray emitted from the light source on the interference filter; a collimator lens for transforming the predetermined wavelength of the measuring ray selected by the interference filter into a parallel measuring ray; an optical mask for splitting the parallel measuring ray into a first split parallel measuring ray and a second split parallel measuring ray; an optical shutter for selectively passing one of the first split parallel measuring ray and the second split parallel measuring ray; a reference means which is provided in a light pass of the first splitting parallel measuring ray; a sample cell which is provided in a light pass of the second split parallel measuring ray; an optical detector or optical receiver for detecting the one of the first split parallel measuring ray which has passed through the reference means and the second split parallel measuring ray which has passed through the sample cell, in order to measure an optical density of a sample in the sample cell; and a second lens for focusing the one of the first split parallel measuring ray which has passed through the reference means and the second split parallel measuring ray which has passed through the sample cell on the optical detector.

In the construction, the optical mask, for example, can be a plate-shaped mask with a pair of apertures for forming the first split parallel measuring ray and the second split parallel measuring ray in which the pair of apertures are juxtaposed symmetrically relative to an optical axis.

In the construction, the measuring ray (or measuring light) emitted from the light source is incident upon the collimator lens after the image of the light source is formed on the interference filter as a spectroscopic filter by means of the first lens; the light is made parallel by the collimator lens; the parallel light is divided or split into the first split parallel measuring ray and the second split parallel measuring ray by means of the optical mask; one of the first split parallel measuring ray and the second split parallel measuring ray is selected by the optical shutter; the one thereof selected by the optical shutter is allowed to pass through either one of the reference means and the sample cell; and the density of the sample is measured and calculated on a basis of an amount of light passing through the reference means, and an amount of light passing through the sample cell.

According to the construction, the optical information upon the light source, namely the predetermined wavelength, selected by the interference filter, of the ray of light that is emitted from each luminous point of the light source is uniformly included in the first and second split parallel measuring rays (i.e. in a pair of split parallel pencils of light).

That is, the information upon fluctuation of the luminous point of the light source, and the positional nonuniformity of the optical penetration characteristics of the interference filter, are uniformly and equally included in both of the pencils of light. As a result, regarding the positional change of the light source which has conventionally been unable to be corrected, by correcting or modifying the equation of operation by means of one-point calibration based on the sample measurement, a high-accuracy measurement can be achieved, thus unnecessary to remake the calibration curve every time the light source is replaced by another light source.

Also, according to the construction, the spectroscopic spectra of both of the pencils of light coincide with each other. Therefore, the fluctuation factors such as the variation in quantity of light emitted from the light source, other than the optical density, is completely cancelled in the reference optical path and the measurement optical path (i.e. sample optical path).

In the above construction, the reference means can include a reference cell. In this construction, it is possible to provide the reference cell and the sample cell as independent separate cells, similar to the conventional cells, in which pure water is put in the reference cell and a sample is put in the sample cell, or in which a sample is put in both the reference cell and the sample cell.

Preferably, the optical density measuring apparatus comprises a single cell housing by which the reference means and the sample cell are constituted, in which the cell housing has a first chamber and a second chamber that penetrate to each other inside, in which a cell length of the first chamber is shorter than a cell length of the second chamber, and in which a reference cell of the reference means corresponds to the first chamber while the sample cell corresponds to the second chamber.

In this construction, the sample is concurrently or simultaneously introduced into the first and second chambers without demarcation. The quantity of light that passes through the reference cell and the quantity of light that passes through the sample cell, differ on a basis of difference in their cell lengths.

According to the construction of the cell, the one single cell is divided by the two chambers into the reference cell and the ample cell; namely, they are not the mutually independent cells. And, the two cells have a positional relation in which the two paraxial split pencils of light penetrate or pass through the cells, and in which both the cells are close infinitely to each other. Also, the sample is concurrently put into the two chambers, and the sample is concurrently discharged from the two chambers. This guarantees that the density of the sample in each of the chambers is identical.

Also, in the construction, the cell is made of a single member as described above. The measuring rays, or the two split parallel pencils of light (i.e. two split parallel measuring rays or lights), travelling from the light source to the optical receiver, pass through the identical optical members. Therefore, the light absorption characteristics of the optical substances other than the density of the sample inside the reference cell chamber and the sample cell chamber, are substantially identical in the detected light that passes through the reference cell and in the detected light that passes through the sample cell, consequently allowing a higher accuracy of measurement to be realized.

As a method to vary the length of one cell, it is simple and convenient to provide an optical refraction adjustment block, such as a block made of glass, in a cell housing having an identical thickness or length. Namely, an optical refraction index adjustment block that has a refractive index equal to or approximate to that of the sample and has a light absorption characteristic different from that of the sample, can be mounted (for example, inserted) in a first portion of the cell through which the aforementioned first splitting parallel pencil of light passes, and the cell length of the first portion thereof is made shorter than the other second portion of the cell by the thickness (i.e. by the length) of the optical refraction index adjustment block.

In other words, the reference means and the sample cell can be constituted by mounting an optical refraction adjustment block partially inside a cell housing with a same length, in which a first chamber formed inside the cell housing has a cell length that is shorter due to intervention of the optical refraction adjustment block than a cell length, generally equal to the same length of the cell housing, of a second chamber formed inside the cell housing, and in which the optical refraction adjustment block has an index of refraction that is similar to an index of refraction of the sample and the optical refraction adjustment block has a light absorption characteristic that is different from a light absorption characteristic of the sample, and wherein a reference cell of the reference means corresponds to the first chamber while the sample cell corresponds to the second chamber.

According to this construction, the two pencils of light penetrating or passing through the first portion and the second portion of the cell (i.e. the light penetrating the reference cell and the light penetrating the sample cell), undergo substantially the same refraction and reach the optical receiver via the second lens.

Therefore, amplification of the displacement (i.e. shift or swerve) of the focusing point (i.e. image-forming point) on the receiver due to aberration of the lens system is effectively prevented, thus improving the accuracy of measurement.

In the construction, the reference means may be a block made of glass.

Alternatively, the reference means may be an atmosphere of air itself.

BRIEF DESCRIPTION OF THE DRAWINGS

These and other objects and features of the present invention will become clear from the following description taken in conjunction with a preferred embodiment thereof and modifications to the embodiment with reference to the accompanying drawings, in which.

DETAILED DESCRIPTION OF THE PREFERRED EMBODIMENT

Figure 1:
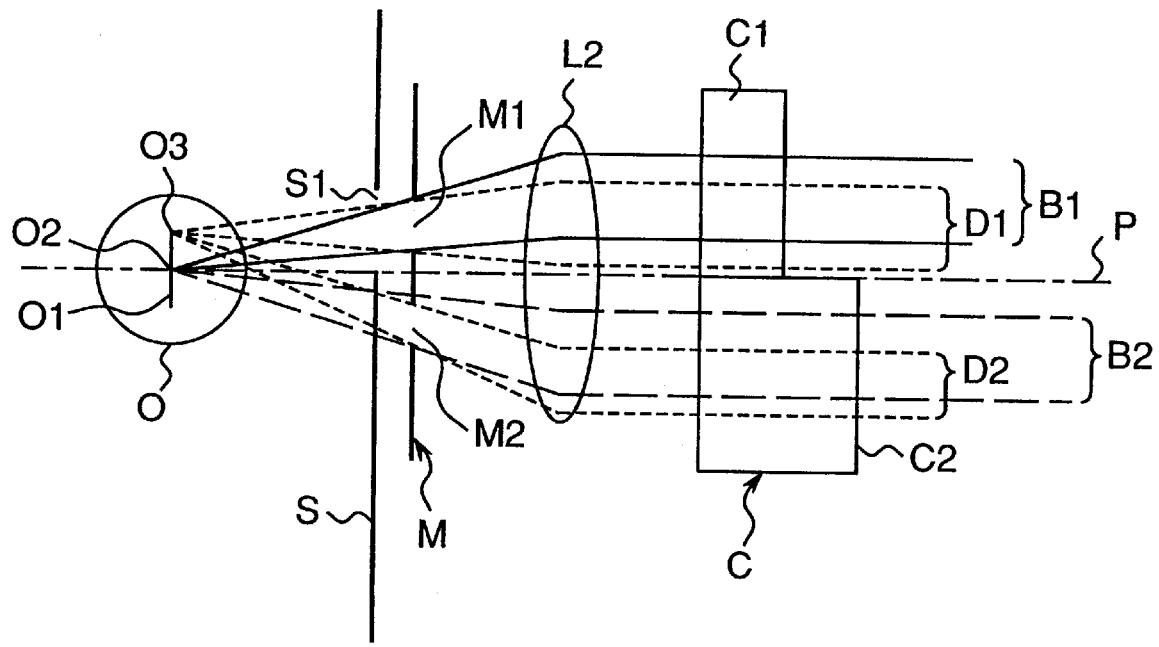
FIG. 1 is an explanatory view of an essential part of a double-beam optical system of a conventional optical density measuring apparatus.

Before a description of the preferred embodiment and modifications thereto proceeds, it is to be noted that like or corresponding parts are designated by like reference numerals throughout the accompanying drawings.

First, referring to FIGS. 3 through 8, the description is made below upon an optical density measuring apparatus according to the preferred embodiment of the present invention.

Figure 3:
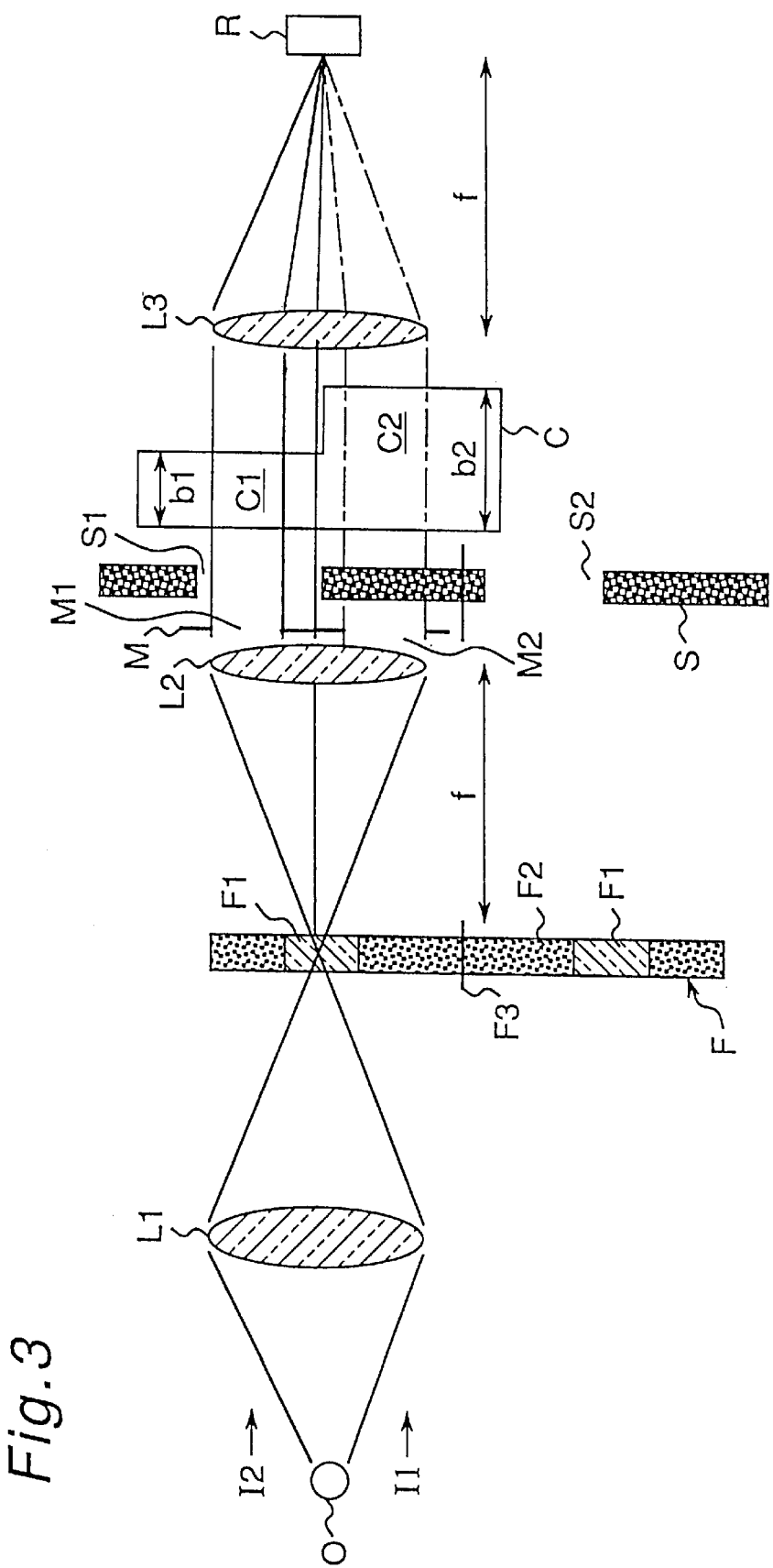
FIG. 3 is an explanatory view of an essential part of an optical system of an optical density measuring apparatus according to a preferred embodiment of the present invention.

FIG. 3 is an explanatory view showing an optical system of the optical density measuring apparatus of the preferred embodiment of the present invention. Referring to FIG. 3, a reference numeral "O" denotes an infrared light source. A measuring light emitted from the light source "O" travels through a measuring area to an infrared light sensor or an optical receiver "R." Optical lenses "L1," "L2" and "L3" are arranged in this order with a line connecting the light source "O" to a center of the optical receiver "R" being as an optical axis, and other optical members are arranged along the optical axis. The measuring light emitted from the light source "O" reaches a focusing lens "L1," and is then focused on an optical filter (interference filter) "F" by the lens "L1". This filter "F" is constituted by a rotation plate "F2" with a specified number of interference filters "F1."

This interference filter "F1" selects only a specified wavelength which is passed through and/or absorbed by a component of the sample to be measured. The rotation plate "F2" has a predetermined number of interference filters "F1" each of which has a particular light absorption characteristic which is selected for each of predetermined plural kinds of samples to be measured. The rotation plate "F2" can rotate about an axis of rotation "F3." The rotation plate "F2" is adjustably rotated about the axis "F3" of rotation so that the light, emitted from the light source "O" and passed through the focusing lens "L1," is focussed on a selected interference filter "F1" of the filter "F."

The infrared measuring light that has penetrated or passed through the interference filter "F1" diffuses again and it reaches the collimator lens "L2." The collimator lens "L2" is positioned ahead of the filter "F" at a location at which the collimator lens "L2" is away from the selected interference filter "F1" with a distance corresponding to a focal length "f" of the collimator lens "L2." With the arrangement, a pencil of light incident on the collimator lens "L2" is sent forward as a parallel light.

Figure 8:
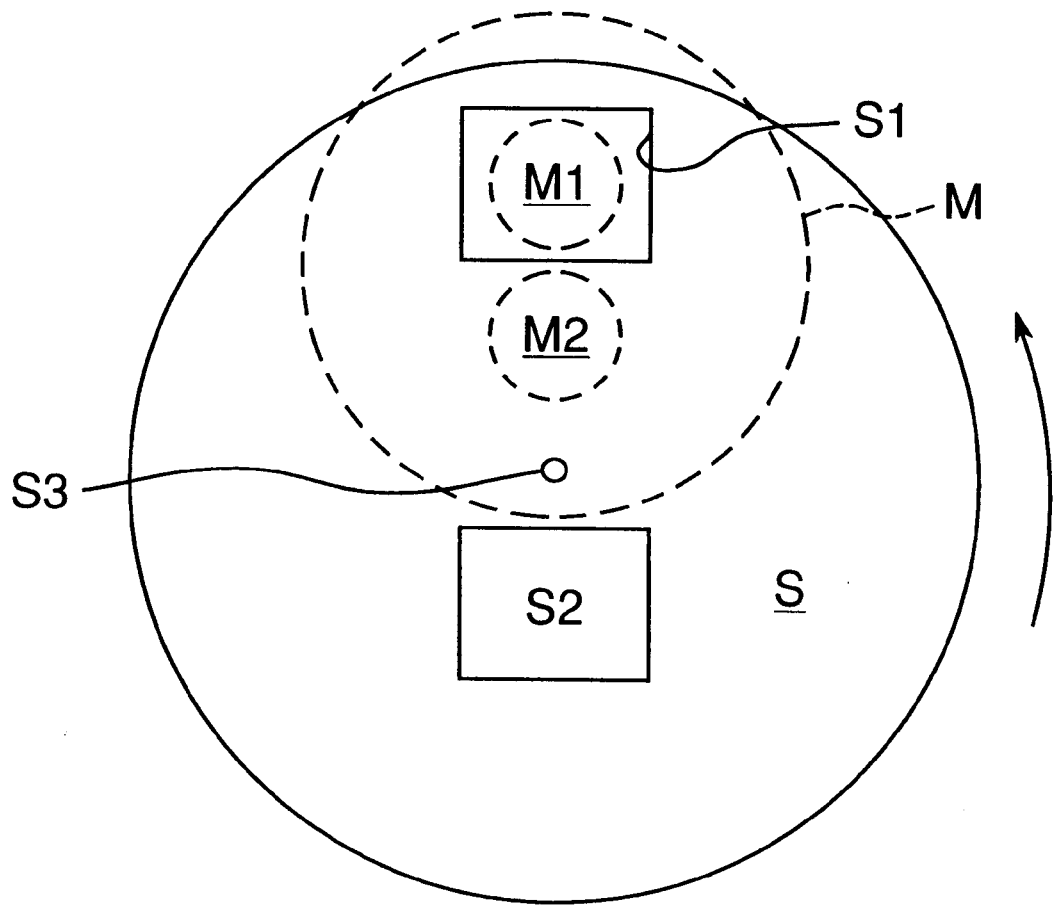
FIG. 8 is a front view of an optical mask and the shutter which are employed in the optical system shown in FIG. 3.

Just ahead of the collimator lens "L2" is arranged an optical mask "M." A front view of the mask "M" is shown in FIG. 8. The mask "M" is provided with a pair of apertures "M1" (which is a "first aperture") and "M2" (which is a "second aperture") so that a distance in diametrical direction between a center (which is coincident with the aforementioned optical axis) of the mask "M" and one "M1" of the apertures "M1" and "M2" is equal to a distance in diametrical direction between the center of the mask "M" and the other "M2" of the apertures "M1" and "M2." The first aperture "M1" is an aperture (i.e. diaphragm) for forming a reference pencil of light; on the other hand, the second aperture "M2" is an aperture (i.e. diaphragm) for forming a sample pencil of light. That is, the parallel light that is formed by the collimator lens "L2" and that corresponds to the lens diameter, is split into a pair of small split parallel pencils of light by the pair of apertures "M1" and "M2." In FIG. 8, the mask "M," the first and second apertures "M1" and "M2," are shown by chain lines, respectively.

Just ahead of the mask "M" is arranged a shutter "S." A front view of this shutter "S" is also shown in FIG. 8. This shutter "S" has a first opening "S1" and a second opening "S2" which are located oppositely and asymmetrically relative to a center "S3" of rotation thereof in its diametrical direction. FIG. 8 shows a state in which the first aperture "M1" of the mask "M" and the first opening "S1" of the shutter "S" are aligned with each other, and the second aperture "M2" of the mask "M" is screened (or closed or blocked) by the shutter "S".

Meanwhile, when the second opening "S2" of the shutter "S" is aligned with the second aperture "M2" of the mask "M", the pencil of light passing through the second aperture "M2" is sent forward, and the first aperture "M1" is screened by the shutter "S."

A cell "C" is arranged in a measuring area provided ahead of the shutter "S." This cell "C" is constituted by integrating the reference cell "C1" with the sample cell "C2" into one cell housing. The reference cell "C1" is arranged on one side of a center thereof (aligned with the optical axis), while the sample cell "C2" is arranged on the other side thereof. A chamber constituting the cell "C1" and a chamber constituting the cell "C2," communicate with each other, and the same sample (liquid) is introduced into both of the chambers.

As shown in FIG. 3, the reference cell "C1" has a cell length of "b1," while the sample cell "C2" has a cell length of "b2." The cell length of the latter is made sufficiently greater than that of the former. The reference pencil of light that has passed through the first aperture "M1" of the mask "M" passes through the reference cell "C1," while the sample pencil of light that has passed through the second aperture "M2" of the mask "M" passes through the sample cell "C2."The aforementioned focusing lens "L3" is arranged ahead of the cell "C," and the aforementioned optical receiver "R" is arranged ahead of the focusing lens "L3" at a location at which the receiver "R" is away from the focusing lens "L3" with a distance corresponding to a focal length "f" of the focusing lens "L3." With the arrangement, the reference pencil of light and the sample pencil of light, which are parallel lights, are focused on the optical receiver "R."

Figure 2:
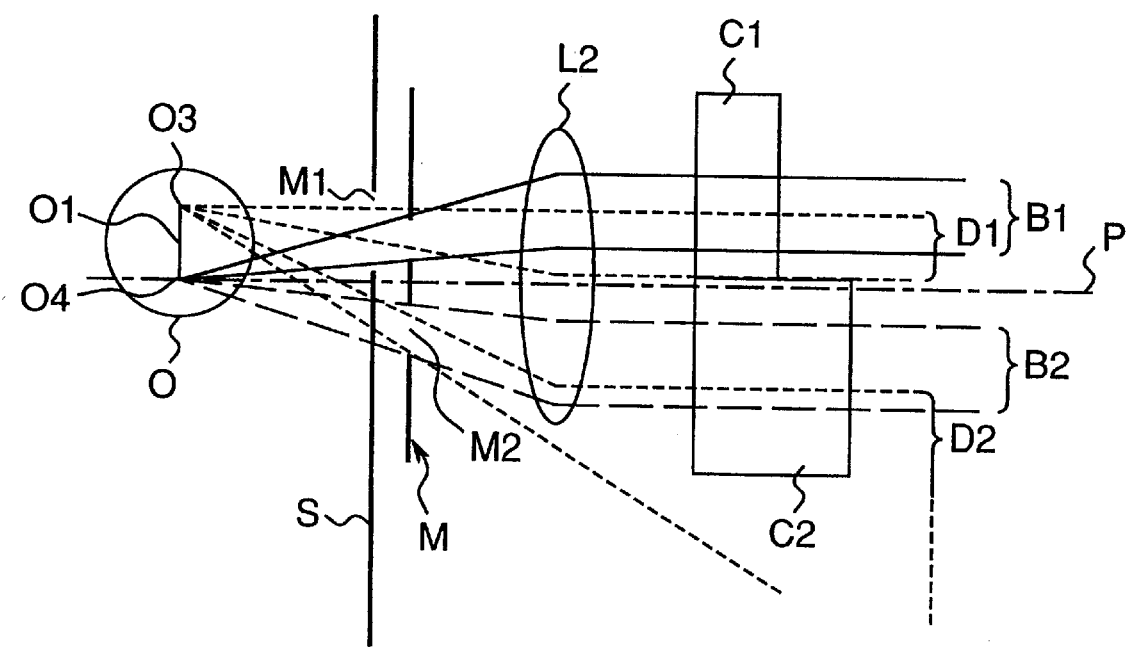
FIG. 2 is an explanatory view similar to FIG. 1.

In comparison with the prior art illustrated in FIGS. 1 and 2, the apparatus of the preferred embodiment has a significant feature that the measuring light is split into the reference pencil of light and the sample pencil of light, only after the light emitted from the light source "O" is transformed into the parallel light by the collimator lens "L2." It is to be noted that, according to the preferred embodiment of the present invention, the measuring light is not split into reference pencil of light and the sample pencil of light, before the light emitted from the light source "O" is transformed into the parallel light by the collimator lens "L2." The effect and function in accordance with the construction of the preferred embodiment will be described below in detail with reference to FIGS. 4 through 7.

Before starting the explanation thereof, a description is made upon a relation between the measurement light and the density, the relation being derived from the Lambert-Beer's Law. The relation is expressed by the following equations (1), (2) and (3):

$$Ib = I1 \times \exp(-a \times b1 \times c) \times \exp(-an \times bn) \times \gamma \quad (1)$$

and $$Is = I2 \times \exp(-a \times b2 \times c) \times \exp(-an \times bn) \times bn) \times \gamma \quad (2)$$

where

I, I1, I2: quantity of light emitted from light source,

Ib: quantity of light received by the optical receiver after passing through the reference cell, Is: quantity of light received by the optical receiver after passing through the sample cell, a: light absorption coefficient, b: cell length (cell thickness), c: density, an: light absorption coefficient of substance other than component to be measured in the measuring optical system (for example, light absorption coefficients of materials forming the cell, the filter and the lens, and light absorption coefficient of dirt adhering upon them), bn: thickness of substance other than component to be measured in the measuring optical system, and γ: fluctuation in detected intensity (fluctuation in sensitivity of the optical receiver, and/or fluctuation in quantity of light).

Based upon the above equations (1) and (2), the density "c" can be obtained by the following equation (3):

$$c = -\ln((Is/Ib) \times (I1/I2))/(a \times (b2-b1)) \quad (3)$$

Figure 5:
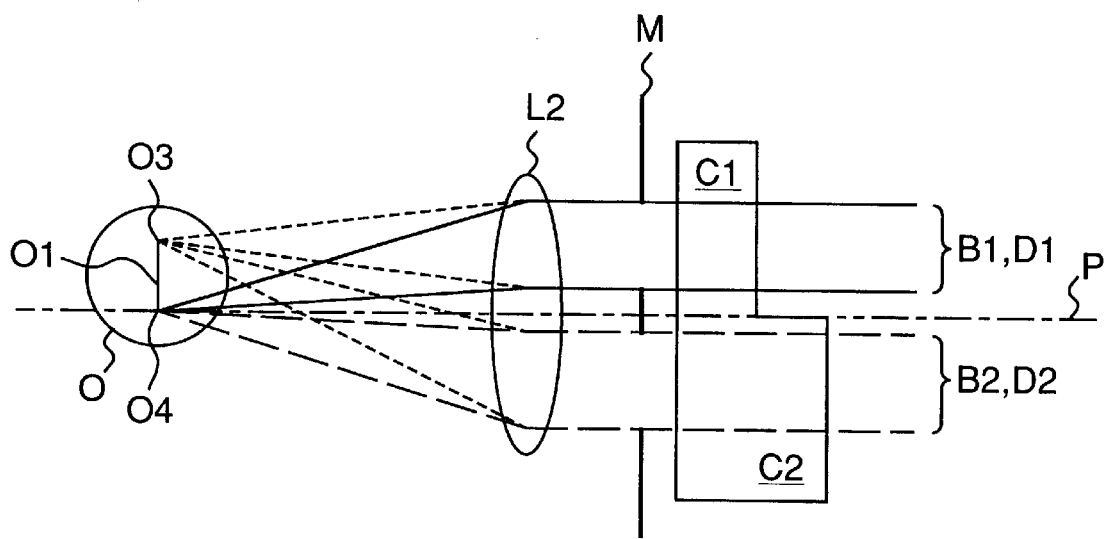
FIG. 5 is an explanatory view similar to FIG. 4, where the shutter and the focusing lens shown in FIG. 3 are omitted.
Figure 6:
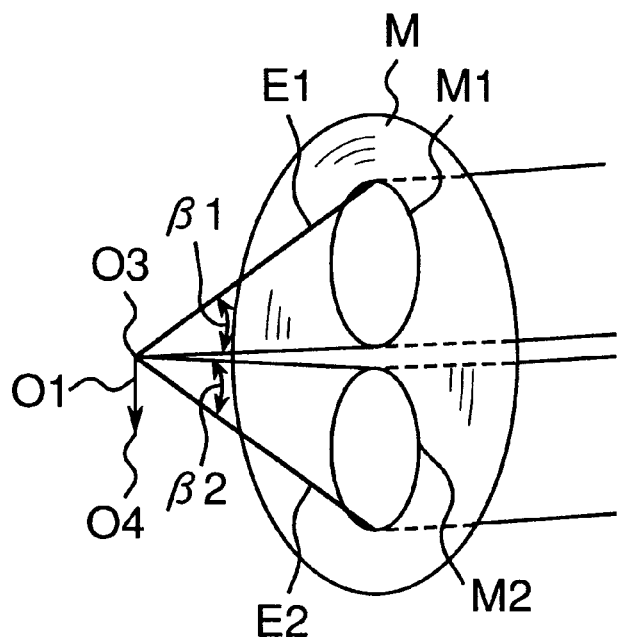
FIG. 6 is an explanatory view showing solid angles of pencils, or beams, of light emitted from a light source.
Figure 7:
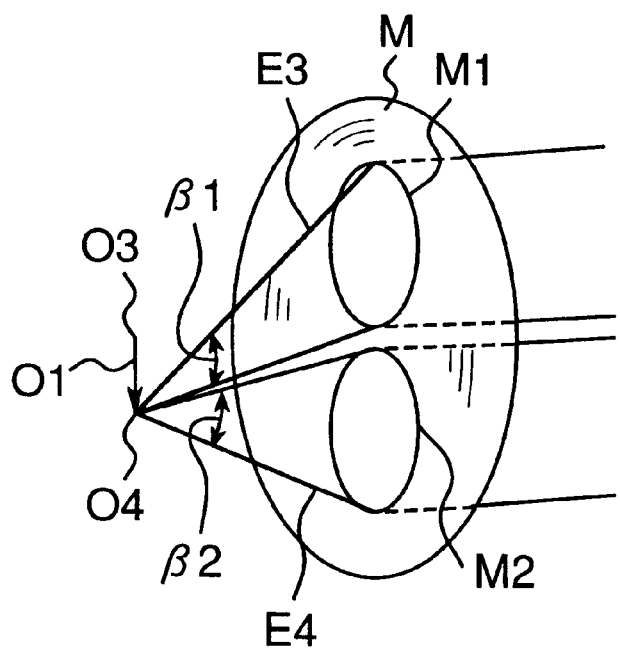
FIG. 7 is an explanatory view similar to FIG. 6.

FIGS. 6 and 7 show fluctuations in solid angle of the pencils of light that are emitted from luminous points of the light source and that are made incident on the apertures "M1" and "M2" of the mask "M"; i.e., the figures show the fluctuations in luminous flux of light or the fluctuations in a unit ray of light. That is, FIGS. 6 and 7 show a state in which one end "O3" of the filament "O1" is located on the optical axis. FIG. 6 illustrates the solid angles of the pencils of light emitted from the end "O3" of the filament "O1", while FIG. 7 illustrates the solid angles of the pencils of light emitted from an end "O4" of the filament "O1". By the way, FIGS. 6 and 7 do not show the focusing lens "L1," the interference filter "F1" and the collimator lens "L2" in comparison with FIGS. 3 through 5.

As shown in FIG. 6, the solid angle "β1" of the pencil of light "E1" (i.e. pencil of light being incident on the aperture "M1") and the solid angle "β2" of the pencil of light "E2" (i.e. pencil of light being incident on the aperture "M2"), both of which are emitted from the luminous point "O3" locating on the optical axis, are equal to each other.

On the other hand, as shown in FIG. 7, the solid angle "β1" of the pencil of light "E3" which is emitted from the luminous point "O4" locating away from the optical axis, and the solid angle "β2" of the pencil of light "E4" which is emitted from the same luminous point "O4" locating away from the optical axis, are, of course, different from each other.

A filament of light source can be considered as an aggregate of such plural luminous points which locate at different positions as described above. Therefore, accurately considering the arrangement shown in FIG. 3, the reference pencil of light and the sample pencil of light do not exactly coincide with each other in terms of light intensity etc. This means that the above "I1" and "I2" do not always coincide with each other.

According to the present embodiment, the measurement light emitted from the light source "O" having a specified area is first focused on the interference filter "F1" of the optical filter "F", and the diffused light from the body of the interference filter "F1" is transformed into the parallel light by the collimator lens "L2." Thereafter, the parallel light is split into the two split parallel pencils of light: the reference pencil of light and the sample pencil of light. Namely, the light emitted from each luminous point of the light source passes through an identical point of the interference filter "F1" and reaches the measurement space.

This will be described in more detail with reference to FIGS. 4 and 5, which corresponds to FIGS. 1 and 2. Although FIGS. 3 and 4 do not show the focusing lens "L1," the optical filter "F" and the shutter "S", it is possible to consider that the illustrated light source filament "O1" is actually superimposed or overlapped on the interference filter "F1".

Figure 4:
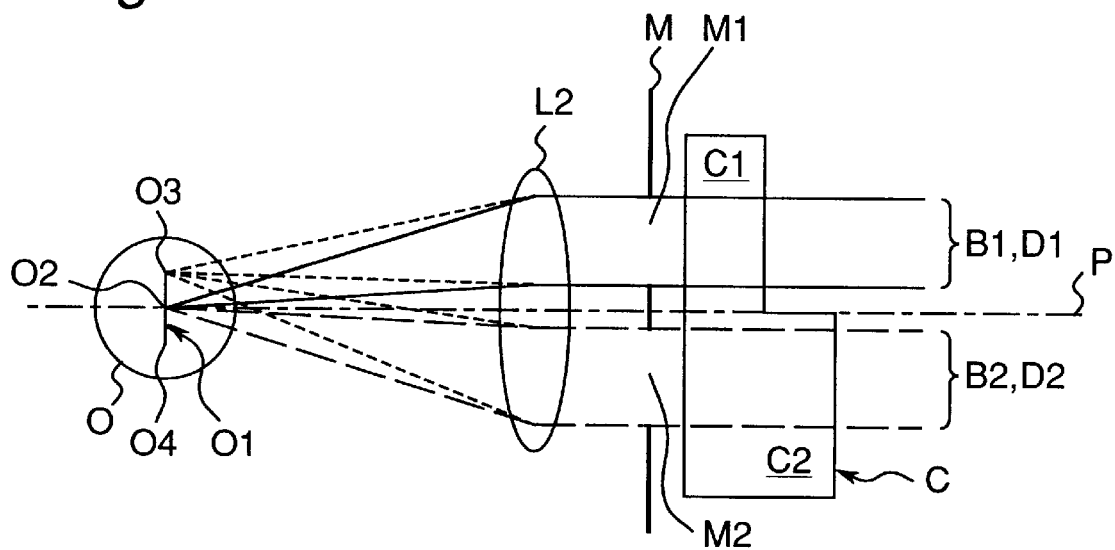
FIG. 4 is an explanatory view showing an operation of the optical system shown in FIG. 3, where a shutter and a focusing lens shown in FIG. 3 are omitted.

In FIG. 4, the center "O2" of the filament "O1", having a specified area, and the center of symmetry of the two apertures "M1" and "M2" of the optical mask "M," are both located on the optical axis "P," which is similar to the case explained above with reference to FIG. 1. With this construction, the measurement light emitted from the point of the center "O2" of the filament "O1" passes through the interference filter "F1" of the filter "Of," passes through the collimator lens "L2" where the light is transformed into the parallel light, and is limited by the pair of mask apertures "M1" and "M2" so that the light is split into two parallel pencils of light "B1" and "B2" symmetrical about the optical axis "P." That is, it can be considered that the two parallel pencils of light "B1" and "B2" are the measuring lights with the same quality in the measuring space in which the cell "C" is positioned.

On the other hand, the measuring light emitted from the end "O3" of the filament "O1" is transformed into the pair of split parallel pencils of light "D1" and "D2" in a similar manner, as shown in FIG. 4. Namely, according to the embodiment, the pencils of light "D1" and "D2" are superimposed or overlapped on the pencils of light "B1" and "B2" to become symmetrical relative to the optical axis "P," different from the conventional optical system explained above with reference to FIGS. 1 and 2. In other words, the lights from the luminous points "O2" and "O3" of the light source are uniformly included in the two split parallel pencils of light.

In addition, it can be appreciated that the difference in spectroscopic characteristics caused by what part of the interference filter "F1" the light passes is also uniformly included in the two split parallel pencils of light in the same manner.

Also, the same thing can be said for the case where the light source itself is replaced by another one and the filament position is changed.

Explaining in more detail, FIG. 5, which corresponds to FIG. 2, shows a state in which the filament position is shifted from the state shown in FIG. 4. Namely, the figure shows that the end "O4" of the filament "O1" is located on the center of the optical axis "P." In this condition, the end "O3," opposite the end "O4," of the filament "O1" is largely displaced or shifted from the center of the optical axis "P." However, the lights emitted from the luminous points "O3" and "O4" are transformed into the parallel lights by the collimator lens "L2." Therefore, the pencils of light "D1" and "D2" emitted from the luminous point "O4" coincide with the pencils of light "B1" and "B2" emitted from the luminous point "O3." As a result, the lights emitted from the luminous points "O3" and "O4" are uniformly included in the two split parallel pencils of light similar to the case shown in FIG. 4.

In the above arrangement, in case that a mask having an aperture of an very small opening is assumed and in case that a unit pencil of light "ΔI" is defined with regard to the pencil of light emitted from each luminous point of the light source, then the quantity of light absorption is uniquely determined with respect to the density in each split optical path.

Regarding the "I1" and "I2," it is nothing but the result indicating how many times (or how many beams of) the unit pencil of light "ΔI" have reached the optical receiver "R" in the optical system. Therefore, the density can be uniquely sought or found from the value of measurement, no matter how the "I1" and "I2" may be varied as a consequence, by calculating the result in terms of the unit pencil of light.

Next, an explanation is made below upon a concrete operation for obtaining the density from the quantity of light in terms of the unit pencil of light "ΔI," based upon the measurement values "I1" and "I2."First, it is explained about the use of this optical density measuring apparatus from the outset.

It is, of course, initially required to execute a blank calibration. Accordingly, the measurement cell "C" (including the reference cell "C1" and the sample cell "C2") is filled with pure water having a density of zero, and then a value of Ib0/Is0 is measured. The measurer cannot directly know the intensity of penetration (or transmission) of the unit pencil of light "ΔI." However, it can be considered that:

"I1"=unit pencil of light ΔI×α; and

"I2"=ΔI×β.

Therefore,

"I1"=(α/β)×I2 can be obtained when I1/I2 is converted into the unit pencil of light.

Therefore, the aforementioned equation (3) can be replaced as follows:

$$c=-\ln((Is/Ib)\times(\alpha/\beta))/(a\times(b2-b1)) \quad (3')$$

Then, K=α/β is obtained by substituting into the equation 3') the measurement values of Ib0 and Is0 satisfying c=0. From the relation, a calibration curve including "K" can be formed, on the assumption that "K" is a constant value.

Namely, the calibration curve is made from the ratio between the quantities of light obtained by multiplying the quantities "ΔI1" and "ΔI2" of lights that penetrate the optical paths of the standard (or reference) unit pencil of light ΔI by "α" and "β," respectively. The density is uniquely determined from the ratio between the quantities "I1" and "I2" of the transmitted light.

Next, it is explained about a case where the light source is replaced by another one so that the quantities of transmitted lights in the two split parallel pencils of light are varied, respectively.

In this case, it is assumed that:

I1' =α'×ΔI; and

I2' =β'×ΔI, where "I1'" and "I2'" are new transmitted pencils of light, respectively.

Under this situation, if measured signal intensities "Ib'" and "Is'" directly applies to the above equation (3'), then the measurement value becomes a value which is different from the true value. For example, the density does not become zero even when pure water is measured, and a different value would be calculated or obtained.

The reason why the values of "I1" and "I1'" become different from each other is due to the difference in quantity between the transmitted pencils of light, and the light absorption characteristics that the unit pencil of light receives, i.e. the quantities I1/α and I1'/α' of the transmitted lights, are the same.

Therefore, under this condition, if the quantities of lights Ib0' and Is0' transmitted or penetrated through pure water are newly measured and substituted into the aforementioned equations (1), (2) and (3'), then there can be obtained the following equations:

$$Ib0' = \Delta I \times \alpha' \times \exp(-a \times b1 \times c) \times \exp(-an \times bn) \times \gamma$$

where c=0;

$$Is0' = \Delta I \times \beta' \times \exp(-a \times b2 \times c) \times \exp(-an \times bn) \times \gamma$$

where c=0; and $$c = -\ln((Is0'/Ib0') \times (\alpha'/\beta'))/(a \times (b2-b1)).$$

According to the above equations, the value of α'/β' can be obtained. And, if "K" in this state is corrected to:

$$K = \alpha'/\beta', \text{ then,}$$

the density can be obtained by means of the calibration curve including "K" that has previously been made, without remaking the calibration curve. This means that the measurement does not receive any substantial influence, by executing the calibration of pure water when the light source is replaced. This also means an overcoming of the fatal drawback of the conventional measuring apparatus of the type with the double-beam optical system.

Next, it is explained about the cell "C."

As described above, the apparatus of the present embodiment employs the cell of the type in which an identical sample is put in an identical cell housing. Therefore, the densities of the samples to be put in the reference chamber and in the sample chamber are, of course, identical. The problem arising in connection with this arrangement is a displacement (i.e. shift or swerve) of a focus being formed on the optical receiver "R," which is caused by a difference in refractive index (or index of refraction) of light due to the difference between the length of the reference cell and the length of the sample cell. Namely, the difference in refractive index between the two optical paths causes a difference between the quantities of refractions of the two pencils of light; consequently, there arises a difference in positions on the optical receiver "R" to which the beams of light reach via the two cells, as a result.

The measurement accuracy and/or variation(s) thereof of the optical receiver "R" is affected by a positional nonuniformity that cannot be actually ignored, and it becomes one of inhibiting factors in the measurement accuracy. It is to be noted that this problem is mostly solved by putting the cell in the path of the parallel light. However, this displacement amounts to about 0.2 mm with respect to a difference of 10 mm in cell length for a measurement wavelength of 1.5 μm according to the present embodiment. Therefore, the spot position of light collected on the optical receiver "R" actually differs, depending on the reference optical path or the measurement optical path. Consequently, the reference accuracy cannot be satisfied for a longer period of time, in a field of measurement use in which its high accuracy is required. This is because the lens in the optical system generates an aberration of the transmitted light; more strictly explaining, this is because the light that has passes the collimator lens "L2" includes a component that is not parallel relative to the optical axis "P". This aberration is a phenomenon that cannot be avoided so long as a general-purpose lens is used in the apparatus.

Figure 9:
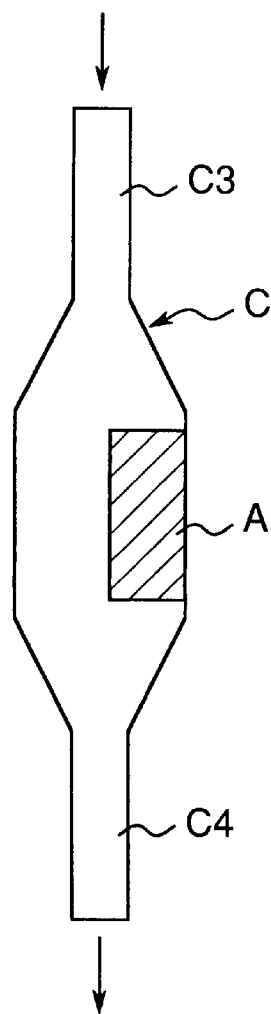
FIG. 9 is a side view showing a cell, according to a first modification, which can be alternatively employed in the optical system shown in FIG. 3.
Figure 10:
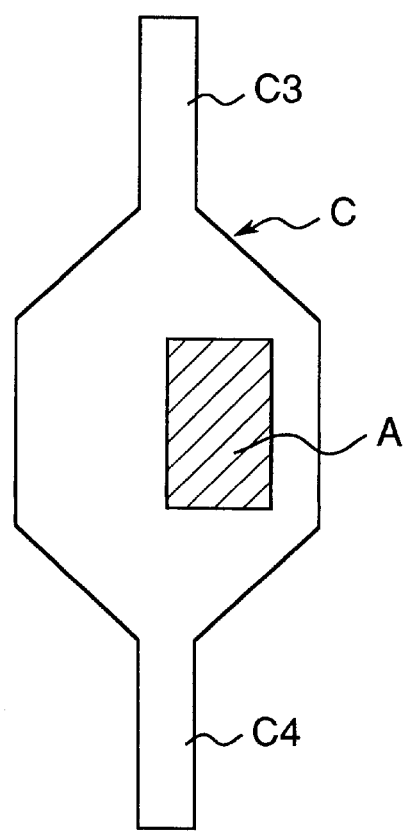
FIG. 10 is a front view of the cell of FIG. 9.
Figure 11:
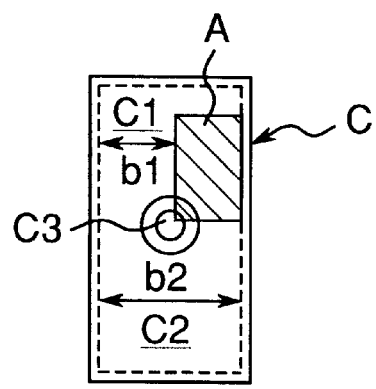
FIG. 11 is a plan view of the cell of FIG. 9.

In order to solve this problem, a first modification of the cell shown in FIGS. 9, 10 and 11 is provided.

Namely, FIG. 11 is a plan view of the cell according to the first modification which corresponds to the drawing of FIG. 3; FIG. 9 is a side view of the cell shown in FIG. 11; and FIG. 10 is a front view of the cell shown in FIG. 11. This cell "C" according to the first modification has a sample inlet "C3" and a sample outlet "C4" at the upper and lower portions of the cell housing, respectively. Inside the cell housing is inserted a refractive index adjustment block "A" having a refractive index identical or approximate to that of the sample (liquid) inside.

That is, the cell length of the reference cell "C1" is "b1," while the cell length of the sample cell "C2" is "b2." However, the housing of the reference cell "C1", and the housing of the sample cell "C2," have the same thickness as shown in FIG. 11, and "cell length b2 minus cell length b1" is the thickness of the block "A."Therefore, with the construction, the pencil of light that has passed through the reference cell and the pencil of light that has passed through the sample cell, undergo a generally same refraction of light.

A normal liquid sample (for example, a semiconductor cleaning liquid) is mostly made of water (refractive index of light: 1.32); therefore, a quartz glass (refractive index of light: 1.45) can be selected as a substance having a refractive index close to that of water.

On the other hand, if the sample is a food oil (refractive index of light: 1.52), then BK7 glass (refractive index of light: 1.51) is appropriate, as another example.

A precondition that these blocks can be employed in the apparatus is that the blocks have a light absorption characteristic different from that of the object component of the sample for the density measurement. By incorporating the aforementioned quartz glass into the cell "C", the focal position swerve of 0.2 mm of the preceding example is substantially reduced to a swerve of not greater than 0.05 mm, thus solving the practical problem in connection with this swerve.

Figure 12:
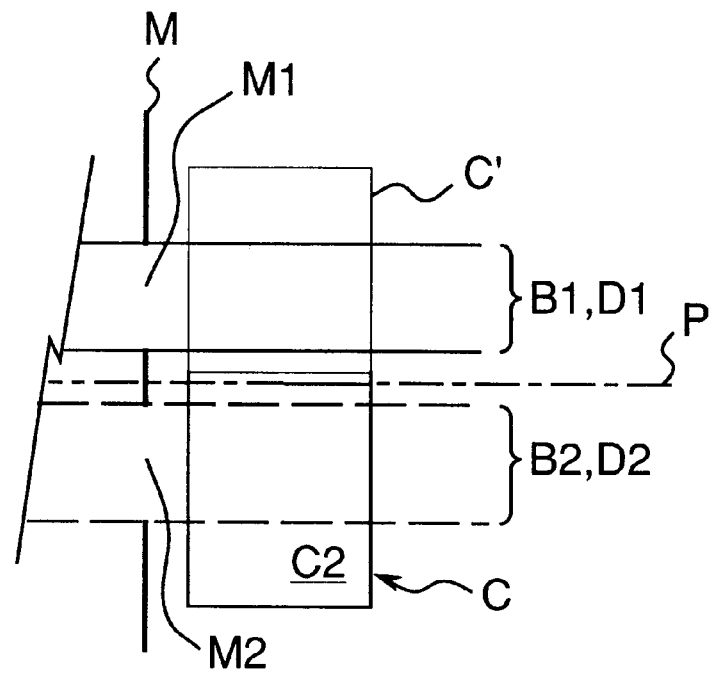
FIG. 12 is a view showing an essential part of a cell, according to a second modification, which can be alrernatively employed in the optical system shown in Fig. 3.

By the way, as a simpler cell construction, it is also possible to provide a quartz glass block "C'" in place of the reference cell C1, as shown in FIG. 12, as a second modification of the cell.

Figure 13:
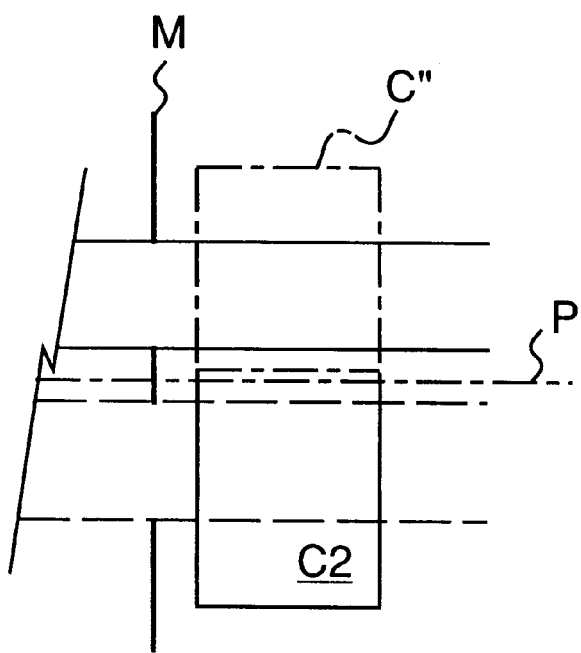
FIG. 13 is a view showing an essential part of a cell, according to a third modification, which can be alternatively employed in the optical system shown in FIG. 3.

Alternatively, it is also possible to provide an atmospheric air "C''" itself in place of the reference cell C1, as shown in FIG. 13, as a third modification of the cell.

Although the present invention has been fully described in connection with the preferred embodiment thereof and modifications to the preferred embodiment with reference to the accompanying drawings, it is to be noted that various other changes and modifications are also apparent to those skilled in the art. Such changes and modifications are to be understood as included within the scope of the present invention as defined by the appended claims unless they depart therefrom.

What is claimed is:

1. An optical density measuring apparatus comprising:
    a light source for emitting an infrared ray as a measuring ray;
    an interference filter for selecting a predetermined wavelength of the measuring ray that passes through the interference filter;
    a first lens for focusing the measuring ray emitted from the light source on the interference filter;

a collimator lens for transforming the predetermined wavelength of the measuring ray selected by the interference filter into a parallel measuring ray;

an optical mask for splitting the parallel measuring ray into a first split parallel measuring ray and a second split parallel measuring ray;

an optical shutter for selectively passing one of the first split parallel measuring ray and the second split parallel measuring ray;

a reference means which is provided in a light pass of the first split parallel measuring ray;

a sample cell which is provided in a light pass of the second split parallel measuring ray;

an optical detector for detecting the one of the first split parallel measuring ray which has passed through the reference means and the second split parallel measuring ray which has passed through the sample cell, in order to measure an optical density of a sample in the sample cell; and a second lens for focusing the one of the first split parallel measuring ray which has passed through the reference means and the second split parallel measuring ray which has passed through the sample cell on the optical detector.

2. The optical density measuring apparatus as claimed in claim 1, wherein the optical mask is a plate-shaped mask with a pair of apertures for forming the first split parallel measuring ray and the second split parallel measuring ray in which the pair of apertures are juxtaposed symmetrically relative to an optical axis.

3. The optical density measuring apparatus as claimed in claim 1, which comprises a cell housing by which the reference means and the sample cell are constituted, in which the cell housing has a first chamber and a second chamber that penetrate to each other inside, in which a cell length of the first chamber is shorter than a cell length of the second chamber, and in which a reference cell of the reference means corresponds to the first chamber while the sample cell corresponds to the second chamber.

4. The optical density measuring apparatus as claimed in claim 1, wherein the reference means and the sample cell are constituted by mounting an optical refraction adjustment block partially inside a cell housing with a same length, in which a first chamber formed inside the cell housing has a cell length that is shorter due to intervention of the optical refraction adjustment block than a cell length, generally equal to the same length of the cell housing, of a second chamber formed inside the cell housing, and in which the optical refraction adjustment block has an index of refraction that is similar to an index of refraction of the sample and the optical refraction adjustment block has a light absorption characteristic that is different from a light absorption characteristic of the sample, and wherein a reference cell of the reference means corresponds to the first chamber while the sample cell corresponds to the second chamber.

5. The optical density measuring apparatus as claimed in claim 1, wherein the reference means is a block made of glass.

6. The optical density measuring apparatus as claimed in claim 1, wherein the reference means is an atmosphere of air itself.

* * * * *

UNITED STATES PATENT AND TRADEMARK OFFICE
CERTIFICATE OF CORRECTION

PATENT NO. : 5,991,031          Page 1 of 5
DATED : November 23, 1999
INVENTOR(S) : Noboru HIGASHI It is certified that error appears in the above-identified patent and that said Letters Patent is hereby corrected as shown below:

In the Abstract,    line 5, delete "the";

line 6, change "occur" to --occurs--.

In Column 1,    line 9, change "which" to --in an infrared optical system. The apparatus--, and change "being" to --including--;

line 10, after "cell" insert --.--, and delete "in an infrared optical system";

line 11, delete "thereof and which", and before "finds" insert --The apparatus--, and after "sample" insert --based--, and delete "a";

line 12, delete "basis of";

line 13, change ", and" to --. The invention--;

line 14, change "the" to --an--;

line 15, delete "therefor";

line 26, delete ",";

line 46, before "time" insert --the--;

line 47, before "time" insert --the--, and after "the" insert --measuring of the--.

UNITED STATES PATENT AND TRADEMARK OFFICE
CERTIFICATE OF CORRECTION

PATENT NO. : 5,991,031

DATED : November 23, 1999

INVENTOR(S) : Noboru HIGASHI

It is certified that error appears in the above-identified patent and that said Letters Patent is hereby corrected as shown below:

| | | |
|---|---|---|
| In Column 2, | line 61, | change "pass" to --passes--. |
| In Column 3, | line 51, | after "to" insert --and--. |
| In Column 5, | line 21, | change "pass" to --path--; |
| | line 22, | change "pass" to --path--; |
| | line 41, | change "by means" to --via--; |
| | line 42, | delete "of"; |
| | line 45, | change "by means of" to --via--; |
| | line 50, | after "calculated" insert --based--, and delete "a"; |
| | line 51, | delete "basis of". |
| In Column 6, | line 2, | change "by means of" to --via--; |
| | line 4, | change ", thus" to --. Thus, it is--; |
| | line 34, | after "differ" insert --based--, and delete "basis of"; |
| | line 38, | delete "the" (second occurrence); |
| | line 42, | change "close infinitely" to --infinitely close--. |

UNITED STATES PATENT AND TRADEMARK OFFICE
CERTIFICATE OF CORRECTION

PATENT NO. : 5,991,031
DATED : November 23, 1999
INVENTOR(S) : Noboru HIGASHI

It is certified that error appears in the above-identified patent and that said Letters Patent is hereby corrected as shown below:

In Column 7,      line 9,    change ", in which a" to --. A--;

line 11, after "length" insert --of a second chamber formed inside the cell housing. The cell length of the second chamber is--;

line 12, delete "same", and delete ", of a";

line 13, delete "second chamber formed inside the cell housing, and in";

line 14, delete "which", and change "the" to --. The--;

line 18, change ", and wherein a" to --. A--.

In Column 8,      line 29, change "being" to --serving--.

In Column 9,      line 5,    delete "and";

line 8,    before "the" insert --and--.

In Column 10,     line 55, change "locating" to --located--;

line 58, change "locating" to --located--;

line 60, change "locating" to --located--;

line 64, after "which" insert --are--, and change "locate" to --located--.

UNITED STATES PATENT AND TRADEMARK OFFICE
CERTIFICATE OF CORRECTION

PATENT NO. : 5,991,031
DATED : November 23, 1999
INVENTOR(S) : Noboru HIGASHI

It is certified that error appears in the above-identified patent and that said Letters Patent is hereby corrected as shown below:

In Column 11,     line 16,     delete ", which corresponds to Figs. 1 and 2";

line 33,     before "symmetrical" insert --which are--;

line 58,     delete ", which corresponds to";

line 59,     delete "Fig. 2,".

In Column 12,     line 8,     change "an" to --a--;

line 63,     change "applies" to --apply--.

In Column 13,     line 27,     change "by means of" to --via--;

line 32,     change "means" to --results in--;

line 35,     delete "it is explained about", change ""C."" to --"C" is explained.--;

line 37,     change "the" (first occurrence) to --a--.

In Column 14,     line 1,     change "passes" to --passed--;

line 25,     delete "a", and after "generally" insert --the--;

line 47,     delete "an".

UNITED STATES PATENT AND TRADEMARK OFFICE
CERTIFICATE OF CORRECTION

PATENT NO. : 5,991,031

DATED : November 23, 1999

INVENTOR(S) : Noboru HIGASHI

It is certified that error appears in the above-identified patent and that said Letters Patent is hereby corrected as shown below:

In Claim 1, Column 15,  line 10,  change "pass" to --path--;

line 12,  change "pass" to --path--;

line 18,  change "a" to --the--;

line 20,  delete "the".

Signed and Sealed this

Twenty-ninth Day of May, 2001

*Attest:*

NICHOLAS P. GODICI

*Attesting Officer*   *Acting Director of the United States Patent and Trademark Office*